United States Patent [19]

Scherrer

[11] 4,124,704

[45] Nov. 7, 1978

[54] 2-NITRO-3-PHENYLBENZOFURAN ALKANOIC (OR PROPENOIC) ACIDS

[75] Inventor: Robert A. Scherrer, White Bear Lake, Minn.

[73] Assignee: Riker Laboratories, Inc., Northridge, Calif.

[21] Appl. No.: 806,526

[22] Filed: Jun. 14, 1977

Related U.S. Application Data

[63] Continuation-in-part of Ser. No. 724,717, Sep. 20, 1976, abandoned, which is a continuation-in-part of Ser. No. 616,277, Sep. 24, 1975, abandoned.

[51] Int. Cl.$^2$ ............................................. C07D 307/82
[52] U.S. Cl. ..................................... 424/180; 424/229; 424/250; 424/269; 424/285; 260/239.6; 260/308 D; 260/346.22; 260/346.73; 536/53; 544/376
[58] Field of Search ..................... 260/346.2 R, 308 D, 260/268 C, 346.73, 239.6; 536/53; 424/285, 229, 250, 269, 180

[56] References Cited

U.S. PATENT DOCUMENTS

| | | | |
|---|---|---|---|
| 3,558,667 | 1/1971 | Mooradian | 260/346.22 |
| 3,682,976 | 8/1972 | Kaltenbronn et al. | 260/346.22 |
| 3,808,236 | 4/1974 | Royer et al. | 260/346.22 |
| 3,862,134 | 1/1975 | Scherrer | 260/346.22 |

FOREIGN PATENT DOCUMENTS 2,081,585  12/1971  France.
2,198,735  9/1972  France.

OTHER PUBLICATIONS

Stoermer, Berichte 44, p. 1853 (1911).
Royer et al., Chimie Therapeutique, Mar.–Apr. 1973, Issue No. 2, pp. 139–142.

*Primary Examiner*—Henry R. Jiles
*Assistant Examiner*—Bernard Dentz
*Attorney, Agent, or Firm*—Cruzan Alexander; Donald M. Sell; Donald C. Gipple

[57] ABSTRACT

Optionally substituted 2-nitro-3-phenylbenzofuranalkanoic and -alkenoic acids which are active as antimicrobial agents, processes for their preparation and intermediates therefor are described.

40 Claims, No Drawings

2-NITRO-3-PHENYLBENZOFURAN ALKANOIC (OR PROPENOIC) ACIDS

This is a continuation-in-part of application Ser. No. 724,717, filed Sept. 20, 1976 and now abandoned, which is itself a continuation-in-part of application Ser. No. 616,277, filed Sept. 24, 1975 (now abandoned) with which Ser. No. 724,717 was copending.

FIELD OF THE INVENTION

This invention relates to a class of 3-phenylbenzofuran compounds which are substituted on the 4, 5, 6 or 7 position of the benzo ring by a lower alkanoic acid group or an ester, amide, acyl halide or pharmaceutically acceptable salt thereof.

BACKGROUND OF THE INVENTION

3-Phenylbenzofuranalkanoic acids and -alkenoic acids and certain derivatives thereof have been reported, for example in U.S. Pat. Nos. 3,682,976 and 3,862,134 as having anti-inflammatory activity. The compound 2-nitro-3-phenylbenzofuran has been reported, although no physiological activity has been reported prior to the present invention. Certain neutral 2-nitrobenzofurans are known as antibacterial agents, for example, see French Patent 2,081,585 and several publications by Rene Royer et al. Acidic compounds combining the structural features of the compounds of the present invention have not previously been described.

SUMMARY OF THE INVENTION

The present invention relates to optionally substituted 2-nitro-3-phenylbenzofuranalkanoic and -alkenoic acids and esters, amides, acyl halides and pharmaceutically acceptable salts thereof which are active as antimicrobial agents.

It is therefore an object of the invention to provide compounds which are active antimicrobial agents.

It is a further object of the invention to provide processes for preparing the compounds of the invention.

It is a further object of the invention to provide a method for controlling microbes.

It is a further object of the invention to provide a method for controlling bacteria.

It is a further object of the invention to provide a method for controlling fungi.

It is a further object of the invention to provide a method for controlling protozoa.

It is a further object of the invention to provide a method for controlling trichomonads.

It is another object of the invention to provide antimicrobial compositions containing 2-nitro-3-phenylbenzofuranalkanoic and -alkenoic acids and esters, amides, acyl halides and pharmaceutically acceptable salts thereof as active ingredients therein.

It is another object of the invention to provide novel intermediates in the preparation of the antimicrobial agents of the invention and processes using the novel intermediates to prepare the active agents.

Still other objects of the invention will be made apparent by the following specification.

DETAILED DESCRIPTION OF THE INVENTION

According to the present invention there is provided a class of compounds of the formula:

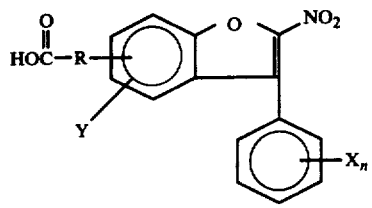

wherein X is halogen, lower alkyl, lower alkoxy, nitro, phenyl, cyano or trifluoromethyl, $n$ is zero, one or two, R is straight or branched chain alkylene of one to four carbon atoms or ethenylene, Y is methyl, methoxy, halogen or hydrogen, or an ester, amide, acid halide or pharmaceutically acceptable salt thereof. When $n$ is zero, the indicated ring positions are unsubstituted. "Lower", when applied to substituent groups herein, refers to groups containing from one to four carbon atoms.

Thus, structurally, the compounds combine an alkanoic or alkenoic acid group, a benzofuran ring, a 2-nitro group on the benzofuran ring and a 3-phenyl group on the benzofuran ring. The free acids are ordinarily white or yellowish to brown crystalline or amorphous materials when purified. They are substantially insoluble in water or aliphatic hydrocarbons and are more soluble in lower alcohols, halogenated solvents, benzene, dimethylformamide and the like. The esters and amides are generally somewhat more soluble in organic solvents. The alkali metal salts have appreciable solubility in water and lower alcohols.

All of the compounds of the invention are active against bacteria and some are also active against other microorganisms, including fungi and protozoa, in vitro and topically. Thus, they can be used for disinfecting and sterilizing, for example of medical and dental equipment, as components of disinfecting solutions. The compounds are particularly useful as antibacterial agents. In general, the compounds are also active in vivo in animals. The free acids are presently preferred for many purposes due to their generally higher levels of antimicrobial activity in vitro. For applications in which water solubility is of importance, the salts are ordinarily used.

The compounds of the invention in which R is methylene (—CH$_2$—) form a presently preferred subclass, due to their high in vivo activity. Other preferred subclasses (due to their high degree of antimicrobial activity) are the compounds in which X is fluorine and/or chlorine and the compounds in which the (4) position of the benzofuran moiety is substituted by hydrogen. The preferred compounds are antimicrobial in vitro and in vivo, are active when administered orally, and provide detectable and antimicrobially active blood levels in mammals. Some of them are active at concentrations of less than 1.0 μg/ml versus *Staphylococcus aureus.* The particularly preferred compounds (which have broad spectra of antibacterial activity and good therapeutic ratios LD$_{50}$/ED$_{50}$) are:

2-nitro-3-phenyl-7-benzofuranacetic acid,
2-nitro-3-phenyl-6-benzofuranacetic acid,
2-nitro-3-phenyl-5-benzofuranacetic acid,
3-(4'-chlorophenyl)-2-nitro-5-benzofuranacetic acid,
3-(4'-fluorophenyl)-2-nitro-7-benzofuranacetic acid,
3-(4'-chlorophenyl)-2-nitro-7-benzofuranacetic acid,
2-nitro-3-phenyl-7-benzofuranacrylic acid, 2-nitro-3-phenyl-5-benzofuranpropionic acid and 2-nitro-3-phenyl-7-benzofuranpropionic acid.

Alkali metal, alkaline earth, aluminum, iron and other metal and amine salts are often the equivalents of the corresponding acid-form compounds, and offer advantages in solubility, absorption, persistence, formulation and the like. The salts are of interest for topical uses (e.g. opthalmic and dermatologic). Alkali metal salts (e.g. Na and K) are preferred. The esters and amides are also useful for modifying solubility, persistence, absorption and other properties. The esters of the invention include lower alkyl esters, hydroxyalkyl esters and N,N-dialkylaminoalkyl esters, glyceryl esters and alkoxyalkyl (particularly methoxymethyl) esters. The amides of the invention include N-unsubstituted amides, N-alkylamides, N,N-dialkylamides, dialkylaminoalkylamides, quaternary ammonium alkylamides, bis(2-hydroxyethyl)-amides, amino acid amides e.g. alanine and glycine amides, carboxyphenylamides, piperazinyl amides, amino sugar amides, alkylsulfonamides, sulfoethylamides, sulfamoylphenylamides and 5-tetrazolylamides.

Among the important subclasses of the compounds of the invention which are represented by specific examples herein are those in which R is methylene, ethylene, methylmethylene or dimethylmethylene; in which X is methyl or methoxy; in which X is fluorine, chlorine or bromine; in which n is one; and in which n is two, and one or both X moieties are halogen, methyl or methoxy. Important subclasses of the compounds other than the free acids which are represented by specific examples herein are lower alkyl esters, hydroxyalkyl esters and N,N-dialkylaminoalkyl esters (particularly ethyl, hydroxyethyl and N,N-dimethylaminoethyl esters), N-unsubstituted amides, dialkylaminoalkylamides, amino acid amides, amino sugar amides and alkylsulfonamides. The ester and amide portions of the compounds of the invention (which replace the OH of the carboxyl function of the free acids) preferably contain not more than ten carbon atoms.

In compounds of the invention wherein R is branched, optically active compounds are obtained which are included within the scope of the invention.

The free acids of the invention are prepared by methods using known starting materials including:

A. the direct nitration of 3-phenylbenzofuranalkanoic and -alkenoic acids,

B. preparing an intermediate 2-halo-3-phenylbenzofuranalkanoic or -alkenoic acid by either (1) the specific halogenation of the 2 position of a 3-phenylbenzofuranalkanoic or -alkenoic acid or (2) the hydrolysis of a 2-halo-3-phenylbenzofuran alkane cyanide followed by the selective displacement of the 2-halogen atom of the intermediate by a nitro group, C. the acid hydrolysis of the corresponding 2-nitro-3-phenylbenzofuran alkane or -alkene cyanide or of the corresponding 2-nitro-3-phenylbenzofuranalkanoic or -alkenoic ester, and D. the reduction of a cyano-3-phenylbenzofuran to the 3-phenylbenzofuranaldehyde followed by halogenation and nitration or direct nitration of the latter to form the 2-nitro-3-phenylbenzofuranaldehyde, reacting that product with acetic anhydride to form the 2-nitro-3-phenylbenzofuranacrylic acid and, if desired, reducing the double bond in the side chain by means of chemical hydrogenation to form the 2-nitro-3-phenylbenzofuranpropionic acid.

The direct nitration process (process A) can be carried out with fuming nitric acid in acetic acid or acetic anhydride or with dinitrogen tetroxide in an inert solvent such as dichloromethane. In order to avoid nitration moderate temperatures of 0° to 30° C. are generally used.

The halogenation step of process B.(1) may be bromination or iodination. The bromination can be carried out using bromine water, N-bromosuccinimide or preferably bromine in a suitable solvent such as dichloromethane or acetic acid. Bromination is carried out under mild conditions, e.g. 0° to 30° C. to avoid aromatic bromination. The bromo compound may be isolated or used without isolation. Isolation may be carried out by extraction, precipitation by the addition of a solvent such as water, evaporation of volatile reaction components, etc. The iodination is carried out e.g. with molecular iodine in the presence of yellow mercuric oxide in an inert solvent such as benzene. Generally these reactions are carried out at about 25° to 125° C., for example at the reflux temperature of the solvent.

Hydrolysis of 2-halo-3-phenylbenzofuranalkane cyanides of process B.(2) is effected under strongly acidic or basic conditions, for example in aqueous sulfuric acid at 60° C. to reflux or in aqueous alcoholic alkali at its reflux temperature.

In the final step of process B, the 2-halo substituent can be displaced by means of selecting nitrating agents, such as strong nitric acid solution, for example 70 percent aqueous nitric acid, dinitrogen tetroxide in e.g. acetic acid or dichloromethane solution or a mixture of sodium nitrite and a strong acid. When 70 percent nitric acid is used as the nitrating reagent for 2-halo derivatives, preferably about two to three moles each of sodium nitrite and nitric acid per mole of benzofuran is included. About four to twenty milliliters of acetic acid per gram of 2-halobenzofuran derivative is used, depending on its solubility. It is desired to maintain the dissolution of the 2-halobenzofuran derivative, and the amount of acetic acid and the reaction temperature are adjusted to achieve this result readily. The reaction temperature is about 25° to 100° C., and preferably about 60° to 80° C. when the halogen is bromine.

It has been found that a mixture of sodium nitrite, sulfuric acid and acetic acid will also nitrate the 2-halobenzofuran derivatives successfully in the 2-position. The 2-halobenzofuran derivative is dissolved in acetic acid to maintain solution (up to 20 ml. per gram required) and concentrated sulfuric acid is added, from two to ten milliliters per gram of benzofuran. Sodium nitrite is then added to the solution. From two to five moles of nitrite per mole of benzofuran derivative is used. The reaction temperature is about 20° to 100° C., and preferably about 55° C. The sodium nitrite can be replaced in this reaction by other metal nitrites such as potassium nitrite.

A combination of nitrogen tetroxide in an inert solvent in the presence of an alkene is one presently preferred nitration method according to process B, with acetic acid and dichloromethane as the preferred solvents. For example, two to five liters of acetic acid per mole of benzofuran or halobenzofuran derivative are generally used. At least one mole of nitrogen tetroxide per mole of benzofuran is used. The exact amount depends on the rate of reaction desired, the extent of volatilization and other physical losses and the amount of competitive addition to the added olefin. An alkene is preferably used with a 2-bromobenzofuran intermediate to remove the elements of BrNO$_2$ and minimize bromination as a side reaction. Cyclohexene is satisfactory for this use. Preferably equimolar amounts of alkene and nitrogen tetroxide are used. The olefin is chosen to be less reactive to N$_2$O$_4$ than the benzofuran but more reactive to BrNO$_2$ than the benzofuran. An acidic olefin, e.g. 3-cyclohexene carboxylic acid is advantageous when the nitrated product is neutral. The temperature of these reactions is generally about 0° to 80° C., preferably 20° to 45° C. for bromine exchange and about 0° to 25° C. for iodine exchange and direct nitration. When 2-iodobenzofurans are used, the olefin is not required (since the iodine is generally unreactive to the benzofuran under the reaction conditions) and only one-half mole of N$_2$O$_4$ is theoretically then required.

The 2-nitro-3-phenylbenzofuranalkanoic and -alkenoic acid esters for use in process C are prepared by nitration of 2-unsubstituted or 2-halo-phenylbenzofuranalkanoic and -alkenoic esters. These esters, preferably lower alkyl esters, are readily hydrolyzed by conventional acid hydrolysis.

The novel 2-nitro-3-phenylbenzofuranalkane cyanides for use in process C are prepared (a) from novel bromomethyl-2-nitro-3-phenylbenzofurans by displacement of bromine with cyanide in inert solvents such as ketones, alcohols and N,N-dimethylformamide, generally at the reflux temperature of the solvent or at about 100° C. or (b) by displacement of halogen from 2-bromo-3-phenylbenzofuranalkane cyanides using techniques and conditions described hereinabove. Hydrolysis of 2-nitro-3-phenylbenzofuranalkane cyanides is effected under strongly acidic or basic conditions, for example in aqueous sulfuric acid at 60° C. to reflux.

The aldehydes which are intermediates in process D are novel compounds of the formula

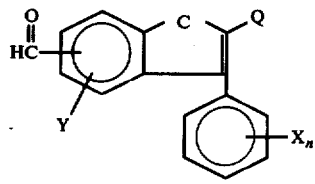

wherein X is halogen, lower alkyl, lower alkoxy, nitro, phenyl, cyano or trifluoromethyl, $n$ is zero, one or two, and Y is methyl, methoxy, halogen or hydrogen, and Q is hydrogen, bromine, iodine or nitro are novel and form an additional part of this invention. These novel intermediates are prepared, for example, from cyano-3-phenylbenzofurans which are known and are prepared by known methods. Preparation is carried out by reaction with aqueous formic acid in the presence of Raney nickel alloy at moderate temperatures, e.g. 50° to 125° C.

The novel 3-phenylbenzofurancarboxaldehydes may be 2-halogenated using the methods of this invention, optionally followed by displacement with a nitro group using the methods of this invention. The novel aldehydes of the invention are also readily converted directly to alkanoic and alkenoic acids of the invention. Condensation of 2-nitro-3-phenylbenzofuranaldehydes with acetic anhydride in the presence of sodium acetate provides a route to 2-nitro-3-phenylbenzofuranacrylic acids, which acids can be reduced to the corresponding propionic acids if desired using chemical hydrogenation.

The pharmaceutically acceptable salts of the invention are readily prepared by reaction of the corresponding free acids with the appropriate base and optionally in a suitable solvent and evaporation to dryness. The base used to prepare the salts may be organic, e.g. sodium methoxide or an amine, or inorganic. Furthermore, other salts which are not pharmaceutically acceptable may be useful for the synthesis of the acid compounds or other acceptable salts or other useful intermediates such as esters. The acyl halides of the invention are prepared by reaction of the free acid with thionyl chloride, generally in a non-reactive solvent such as dichloromethane or benzene. The esters of the invention are prepared as described above in connection with their use in process C. The amides are generally prepared by reaction of the acyl halides (especially acyl chlorides) of the free acids of the invention with the desired amines. The free acids can also be prepared from the corresponding esters, amides and acyl halides by methods known to those skilled in the art.

The antimicrobial activity of the compounds is evaluated using a variation of the original agar-plate diffusion method of Vincent and Vincent (e.g. see Vincent, J. G., and Vincent, Helen W., Proc. Soc. Exptl. Biol. Med. 55:162–164, 1944, and Davis, B. D., and Mingioli, E. S., J. Bac. 66:129–136, 1953. Using this test, the compounds of the invention have been found to have a broad spectrum of activity against both gram-positive and gram-negative microorganisms. The procedure provides information on the amount of a compound required to give complete inhibition, partial inhibition or no inhibition of microbial growth on agar plates. The microbial growth on each plate is read visually, and minimal inhibitory concentrations are recorded.

The microorganisms used are:
1. *Staphylococcus aureus*
2. *Bacillus subtilus*
3. *Pseudomonas aeruginosa*
4. *Escherichi coli*
5. *Streptococcus sp.* [1]
6. *Aspergillus niger*
7. *Candida albicans*
8. *Mima polymorpha*
9. *Herellea vaginicola*
10. *Klebsiella pneumoniae*
11. *Streptococcus fecaelis*

[1]Strains isolated from dental caries in rats or hamsters at the National Institute of Dental Health and grown in PFY or APT agar.

These are selected representatives of various bacterial and fungal classes, and broad spectrum activity can be predicted as a result of activity against them. All of the compounds of the invention possess antimicrobial activity towards one or more of the above microorganisms. The compounds maintain high activity against the microorganisms either in the absence or presence of ten percent horse serum.

The in vivo antimicrobial activity is determined against infections produced by *Streptococcus pyogenes* C-203 and *Staphylococcus aureus* (Smith) or other bacterial species. The species used is determined by the in vitro antimicrobial spectrum of the compound. Groups of five or ten mice, 18–22 g., are infected intraperitoneally with the test culture. Treatment consists of three oral injections one, six and twenty-four hours after infection. All mice are observed for extended periods, e.g. for two weeks, and deaths are recorded at daily intervals. Control groups consist of one infected, nontreated group and other infected groups receiving varying dosages of the reference standard.

The acute oral toxicity of the compounds of the invention generally is moderate to low compared with the effective oral dose, and they have a good to excellent therapeutic ratio.

The compounds of the invention may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about five parts per thousand are suitable, and the formulation is used by immersing the object to be treated therein, or by local application to an infected area. The amount of compound to be used for e.g. oral treatment of a microbial infection will be an effective amount less than a toxic amount. The amount to be administered to a subject and route of administration to control an infection will depend on the species of organism, the sex, weight, physical condition of the patient, the locus of the infection and many other factors, but this judgment is well within the skill of the art. Usually the amount will be less than 100 mg/kg per dose. Conveniently the oral treatment is administered in the form of the usual pharmaceutical preparation such as capsules, tablets, emulsions, solutions, suppositories and the like. Excipients, fillers, coatings, etc. are employed with tablets or capsules, as is well known in the art.

It is often advantageous to combine the compounds of this invention with other antimicrobial compounds such as coccidiostats, anthelmintics, antifungals, antibiotics, steroids or antibacterial agents, or to combine more than one compound described herein in a single composition.

Certain of the compounds are also active antiparasitics as shown by activity in laboratory tests versus the protozoan Trichomonas sp. In view of the outstanding antimicrobial activity of the compounds, they would also be expected to be effective growth promoters in various animal and bird species.

The following examples are given for the purpose of further illustrating the procedures of the present invention, but are not intended, in any way, to be limiting on the scope thereof. Thus, while the majority of the examples relate to the free acid compounds, the other compounds of the invention can also be prepared. The melting points are uncorrected, the temperatures are in degrees Centigrade and the pressures in millimeters of mercury.

EXAMPLE 1

A prepared mixture of 15 ml. of acetic acid and 10 ml. of yellow fuming nitric acid is cooled to about 10° C. in an ice bath, and 4.8 g. (0.019 mole) of 3-phenyl-6-benzofuranacetic acid (shown at column 18, line 1, of U.S. Pat. No. 3,862,134) is added with stirring. This mixture is stirred at room temperature for about one hour and then poured onto ice. A yellow solid precipitate which forms is extracted into diethyl ether. The ether solution is washed with saturated sodium chloride solution, with water, and then with the sodium chloride solution again. The solution is dried over sodium sulfate, and the ether is removed by evaporation under vacuum. The residue is a yellow solid which is recrystallized twice from a mixture of ethanol and water, then from a mixture of benzene and hexane to provide a yellow powder. This product is 2-nitro-3-phenyl-6-benzofuranacetic acid, m.p. 187°–191° C.

| Analysis: | % C | % H | % N |
|---|---|---|---|
| Calculated for $C_{16}H_{11}NO_5$: | 64.7 | 3.73 | 4.7 |
| Found: | 64.3 | 3.60 | 4.7 |

EXAMPLE 2

To a solution of 14.0 g. (0.055 mole) of 3-phenyl-7-benzofuranacetic acid (shown at column 17, line 63, of U.S. Pat. No. 3,862,134) in 150 ml. of acetic acid is added 8.9 g. (0.055 mole) of bromine dropwise with stirring. After about one hour a precipitate begins to appear, and the mixture is heated to 45° C. to maintain solution of the product which is 2-bromo-3-phenyl-7-benzofuranacetic acid. Rather than isolating this product, it is used as is. A solution of 7 ml. of concentrated sulfuric acid in 50 ml. of acetic acid is added to the reaction mixture. Next, 13.8 g. (0.2 mole) of solid sodium nitrite is added in small portions over a period of eight minutes while maintaining the reaction temperature at about 55° C. The mixture is heated at 55° C. for about two hours and is then poured into ice water. The precipitate which forms is extracted into diethyl ether, which is washed with water and sodium chloride solution. The ether extracts are then dried over sodium sulfate, filtered to remove the sodium sulfate, and evaporated to dryness under vacuum. The residue is crystallized by suspending in a small amount of diisopropyl ether. The product precipitate is a solid which is recrystallized twice from benzene, then twice from ethanol. The yellow product is 2-nitro-3-phenyl-7-benzofuranacetic acid, m.p. 170°–173° C.

| Analysis: | % C | % H | % N |
|---|---|---|---|
| Calculated for $C_{16}H_{11}NO_5$: | 64.7 | 3.7 | 4.7 |
| Found: | 64.5 | 3.6 | 4.6 |

EXAMPLE 3

To a mixture of 5.4 g. (0.02 mole) of 3-(4-fluorophenyl)-7-benzofuranacetic acid (shown in Example 9 of U.S. Pat. No. 3,862,134) in 150 ml. of chloroform (stabilized with ethanol) is added dropwise 3.2 g. (0.02 mole) of bromine. The mixture is stirred for about 16 hours, then evaporated. The residue is extracted with petroleum ether, then the ether is evaporated to provide a white solid. The solid is recrystallized from hexane to provide ethyl 2-bromo-3-(4-fluorophenyl)-7-benzofuranacetate, m.p. 63°–67° C.

To a solution of 3.8 g. (0.0101 mole) of ethyl 2-bromo-3-(4-fluorophenyl)-7-benzofuranacetate in 30 ml. of acetic acid is added 2 ml. of 70 percent nitric acid and then 4 g. (0.0202 mole) of solid sodium nitrite in small portions over about 1½ minutes. The mixture is stirred while heating gradually over 1¼ hours to about 80° C., allowed to cool, and poured into water. The ether extracts are washed with water and twice with saturated sodium chloride solution. The ether extracts are then dried over sodium sulfate, filtered to remove the sodium sulfate and evaporated under vacuum to provide an orange residue. The product is separated from this residue by chromatography on neutral alumina. Elution is carried out by using a one to one mixture of hexane and benzene followed by two portions of benzene. The desired product elutes rapidly and is completely eluted by the benzene. The fractions eluted by benzene are recrystallized from carbon tetrachloride. The product is a white solid, ethyl 3-(4-fluorophenyl)-2-nitro-7-benzofuranacetate, m.p. 103°-104.5° C.

| Analysis: | % C | % H | % N |
|---|---|---|---|
| Calculated for $C_{18}H_{14}FNO_5$: | 63.0 | 4.1 | 4.1 |
| Found: | 62.6 | 4.0 | 4.0 |

EXAMPLE 4

In 200 ml. of glyme are placed 28.6 g. (0.159 mole) of ethyl (4-hydroxyphenyl)acetate, 37.2 g. (0.159 mole) of 4-chloro-α-bromoacetophenone and 28.6 g. of potassium carbonate. The mixture is heated at its reflux temperature for five hours, then diluted with water and diethyl ether. The ether layer is washed with water, cold 0.5N sodium hydroxide solution and saturated sodium chloride solution and treated with decolorizing charcoal, then dried. The solution is evaporated to provide a residue which is recrystallized from methanol yielding 24.4 g. of yellow crystals of condensation product, m.p. 87°-92° C. This product is mixed with 165 g. of polyphosphoric acid and heated at 110° C. for 1.5 hours. The mixture is poured into ice and water. This mixture is extracted with diethyl ether. The ether layer is washed with water and saturated sodium chloride solution, then dried. Evaporation provides 20.7 g. of ethyl 3-(4-chlorophenyl)-5-benzofuranacetate. This ester is hydrolyzed in 210 ml. of ethanol with 21 ml. of water and 20.7 g. of sodium hydroxide by heating at reflux for two hours. The solution is evaporated, and the residue is partitioned into water and diethyl ether. The water layer is poured into cold dilute hydrochloric acid to provide a yellow, gummy solid. The solid is dissolved in diethyl ether. The ether layer is washed with water and saturated sodium chloride solution, then dried. Evaporation provides a solid which is recrystallized twice from aqueous ethanol, then from benzene to yield 3-(4-chlorophenyl)-5-benzofuranacetic acid, m.p. 136°-140° C.

| Analysis: | % C | % H |
|---|---|---|
| Calculated for $C_{16}H_{11}ClO_3$: | 67.0 | 3.87 |
| Found: | 67.3 | 3.70 |

To a solution of 3-(4-chlorophenyl)-5-benzofuranacetic acid (9.7 g., 0.034 mole) in 100 ml. of chloroform is added dropwise with stirring a solution of 5.4 g. (0.034 mole) of bromine in 15 ml. of chloroform dropwise over one-half hour. Stirring is continued for an additional two hours. The reaction mixture is then evaporated under vacuum to provide 2-bromo-3-(4-chlorophenyl)-5-benzofuranacetic acid, a green solid, m.p. 152°-165° C.

The 2-bromo compound is mixed without further purification with 106 ml. of acetic acid, and the mixture is warmed until solution is obtained. The mixture is allowed to cool to room temperature, then 56 ml. of 70 percent nitric acid are added. To this mixture is added sodium nitrite (4.7 g., 0.068 mole) in small portions. The mixture is heated at 80° C. over a period of one hour. The mixture is then poured into cold water. The yellow solid product is separated by filtration and washed with water. After three recrystallizations from 95 percent ethanol the product, 3-(4-chlorophenyl)-2-nitro-5-benzofuranacetic acid, is a yellow powder, m.p. 211° C. (dec.).

| Analysis: | % C | % H | % N |
|---|---|---|---|
| Calculated for $C_{16}H_{10}ClNO_5$: | 57.9 | 3.04 | 4.22 |
| Found: | 58.3 | 3.00 | 3.80 |

EXAMPLE 5

To a solution of 3.85 g. (0.0775 mole) of sodium hydride in 150 ml. of glyme is added 18 g. (0.0775 mole) of 7-cyanomethyl-3-phenylbenzofuran (shown at column 17, line 31, of U.S. Pat. No. 3,862,134), and the mixture is heated to its reflux temperature and maintained at reflux for about one hour. The solution is then cooled with an ice bath and 33 g. (0.23 mole) of methyl iodide is added slowly. The reaction mixture is stirred for about sixteen hours at about 21° C. To the mixture is added a few milliliters of ethanol, then it is evaporated to dryness. Diethyl ether and water are added and mixed thoroughly. The ether layer is washed with saturated sodium chloride solution, dried, then evaporated to provide an oil.

This oil is dissolved in 200 ml. of ethanol, 40 g. of potassium hydroxide are added, and the mixture is heated at its reflux temperature for about sixteen hours. The mixture is partially evaporated, and the concentrate is extracted with a mixture of diethyl ether and hexane. The organic fraction is evaporated to provide an oil. The oil is extracted with hexane. The extracts are evaporated to provide a residue which is further hydrolyzed by dissolving it in 100 ml. of ethylene glycol with 10 g. of 85 percent potassium hydroxide and heating the mixture at 130° C. for sixteen hours. The product is isolated by evaporating to provide a residue, extracting the residue with diethyl ether and hexane and acidifying the aqueous layer to give a white solid which is dissolved in diethyl ether. The ether layer is washed with water, dried, then evaporated. The residue is recrystallized from a benzene-hexane mixture, then from aqueous ethanol to provide off-white crystals of α,α-dimethyl-3-phenyl-7-benzofuranacetic acid, m.p. 169°-171° C.

| Analysis: | % C | % H |
|---|---|---|
| Calculated for $C_{18}H_{16}O_3$: | 77.1 | 5.75 |
| Found: | 76.8 | 5.50 |

Bromination of this compound using the method of Example 4 provides 2-bromo-α,α-dimethyl-3-phenyl-7-benzofuranacetic acid, m.p. 183°-196° C. Further reaction of this intermediate product, also using the method of Example 4, provides α,α-dimethyl-2-nitro-3-phenyl-7-benzofuranacetic acid, m.p. 256.5°-258.5° C. The compounds of Examples 6-8, shown in Table I, are also prepared according to the method of Example 4. The starting materials therefor are shown in U.S. Pat. No. 3,862,134, respectively at column 18, lines 12-13, in Example 5, and in Example 9. In cases where the intermediate 2-bromo compound has been isolated, the melting point is given.

TABLE I

| Example No. | Intermediate Bromo Compound | Final Product | Melting Point (° C). |
| --- | --- | --- | --- |
| 6 | 2-bromo-3-(4-chlorophenyl)-7-benzofuranacetic acid | 3-(4-chlorophenyl)-2-nitro-7-benzofuranacetic acid | 233–235 |
| 7 | 2-bromo-α-methyl-3-phenyl-7-benzofuranacetic acid, m.p. 153.5–155.5° C. | α-methyl-2-nitro-3-phenyl-7-benzofuranacetic acid | 178–180 |
| 8 | 2-bromo-3-(4-fluorophenyl)-7-benzofuranacetic acid, m.p. 169–170° C. | 3-(4-fluorophenyl)-2-nitro-7-benzofuranacetic acid | 191–194.5 |

EXAMPLE 9

To a stirred solution of 18.2 g. (0.72 mole) of 3-phenyl-5-benzofuranacetic acid (shown at column 17, line 65, of U.S. Pat. No. 3,862,134) in 400 ml. of dichloromethane is added 8.2 g. (0.10 mole) of sodium acetate and then, dropwise, a solution of 11.5 g. (0.072 mole) of bromine in 25 ml. of dichloromethane. After one hour the addition of the diluted bromine is stopped with 3.2 ml. of solution remaining. The solution is allowed to stir for about 1½ hours additional. The reaction mixture is washed with water, with 10 percent aqueous sodium bisulfite, then again with water. The dichloromethane fraction is then dried over magnesium sulfate and filtered to remove the magnesium sulfate. The resulting solution is concentrated under vacuum to provide 2-bromo-3-phenyl-5-benzofuranacetic acid, a white powder, m.p. 130°–140° C. This solid is used without further purification. A mixture of 23.8 g. (0.072 mole) of 2-bromo-3-phenyl-5-benzofuranacetic acid in 250 ml. of acetic acid is warmed to achieve solution, then allowed to cool to room temperature. To this solution is added 8.9 g. (0.108 mole) of cyclohexene and then, dropwise, a solution of 9.9 g. (0.108 mole) of dinitrogen tetroxide in 25 ml. of acetic acid. After the solution has stirred for a period of three hours, the precipitate which has formed is collected by filtration, washed with cold acetic acid, with water and finally with petroleum ether. The yellow-green solid product is recrystallized twice from 95 percent ethanol and once from isopropyl alcohol to provide a yellow crystalline solid, 2-nitro-3-phenyl-5-benzofuranacetic acid, m.p. 209°–212° C.

| Analysis: | % C | % H | % N |
| --- | --- | --- | --- |
| Calculated for $C_{16}H_{11}NO_5$: | 64.6 | 3.7 | 4.7 |
| Found: | 64.3 | 4.0 | 4.5 |

EXAMPLE 10

A solution of 2 g. of 2-nitro-3-phenyl-5-benzofuranacetyl chloride (shown in the first paragraph of Example 30 hereof) in 75 ml. of benzene is treated with gaseous ammonia. A precipitate forms rapidly and is separated by filtration. Recrystallization from 95 percent ethanol provides yellow solid 2-nitro-3-phenyl-5-benzofuranacetamide, m.p. 220.5°–222.5° C.

The compounds of the following table, which are representative of the amino sugar amides, dialkylaminoalkyl amides, amino acid amides and alkylsulfonamides of the present invention, are prepared using the synthetic method described in Example 10 starting with 2-nitro-3-phenyl-5-benzofuranacetyl chloride and the appropriate known amine or amide salt.

TABLE II

| Product | Melting Point (° C) |
| --- | --- |
| [structure] | 206–207 (dec.) |
| [structure] | 183–185 |

TABLE II-continued

| Product | Melting Point (° C) |
|---|---|
| 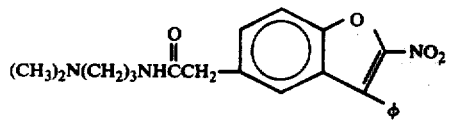 | 159.5–161.5 |
| 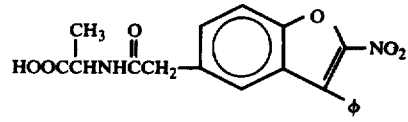 | 199–201 |
| 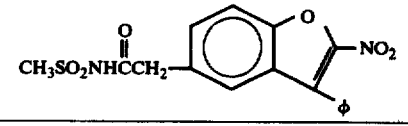 | 219.5–221.5 |

EXAMPLE 11

To a solution of 16.1 g. (0.060 mole) of 3-phenyl-5-benzofuranpropionic acid (shown in Example 16 of U.S. Pat. No. 3,862,134) in 300 ml. of dichloromethane is added sodium acetate (8.2 g., 0.10 mole), then a solution of bromine (9.6 g., 0.06 mole) in 25 ml. of dichloromethane. The mixture is stirred for a total of two hours, then washed with water, 10 percent sodium bisulfite solution and water, and finally with saturated sodium chloride solution. The dichloromethane fraction is then dried and concentrated to provide a tan solid, 2-bromo-3-phenyl-5-benzofuranpropionic acid, crude m.p. 70°–80° C. This product is used without further purification for the next step.

To a solution of 2-bromo-3-phenyl-5-benzofuranpropionic acid (20.7 g., 0.060 mole) in 250 ml. of acetic acid is added 7.4 g. (0.090 mole) of cyclohexane, then, dropwise, 8.3 g. (0.090 mole) of dinitrogen tetroxide in 25 ml. of acetic acid. After stirring a total of three hours the misture is poured into cold water, then extracted with eleven 100 ml. portions of cold 0.5N sodium hydroxide solution. Extracts 7 through 11 are combined and poured into cold dilute hydrochloric acid. The crude product is taken up in diethyl ether, the ether extracts are washed with water and saturated sodium chloride solution, then dried and concentrated to provide a tan residue. The product is purified by chromatography on 40 to 140 mesh silica gel (about 200 g.). The column is eluted with chloroform containin 1 percent acetic acid. The first 1050 ml. of eluate is evaporated to a yellow solid which is recrystallized from 95 percent ethanol, then from benzene to provide yellow crystals of 2-nitro-3-phenyl-5-benzofuranpropionic acid, m.p. 174°–178° C.

| Analysis: | % C | % H | % N |
|---|---|---|---|
| Calculated for $C_{17}H_{13}NO_5$: | 65.7 | 4.2 | 4.5 |
| Found: | 65.7 | 4.1 | 4.5 |

EXAMPLE 12

Using the method of Example 11, 3-phenyl-7-benzofuranpropionic acid (i.e. 3-[7-(3-phenylbenzofuran)]-propionic acid as shown in the second paragraph of Example 12 of U.S. Pat. No. 3,862,134) is brominated to provide 2-bromo-3-phenyl-7-benzofuranpropionic acid, m.p. 182°–183.5° C.

A mixture of 2-bromo-3-phenyl-7-benzofuranpropionic acid (7.0 g., 0.0203 mole) and 400 ml. of acetic acid is warmed to effect solution. Cyclohexene (2.05 g., 0.025 mole) is added, followed by dropwise addition of dinitrogen tetroxide (2.3 g., 0.025 mole) in 10 ml. of acetic acid. The solution is heated at 55° C. for about one-half hour. An additional 0.5 g. of dinitrogen tetroxide dissolved in 5 ml. of acetic acid is added dropwise at this time, then the mixture is heated at 55° C. for another hour. The mixture is then cooled and added to an ice water mixture. The precipitate is separated by filtration. The product is dissolved in dilute sodium hydroxide, and the solution is treated with decolorizing charcoal, and the product is precipitated with dilute hydrochloric acid. The precipitate is extracted into chloroform (about 2 liters) then the chloroform extracts are dried over magnesium sulfate. The extracts are filtered to remove the magnesium sulfate and evaporated under vacuum. The residue is recrystallized twice from ethanol with concomitant treatment with decloroizing charcoal, then recrystallized once from methanol, again treating with decolorizing charcoal. The product is a yellow solid, 2-nitro-3-phenyl-7-benzofuranpropionic acid, m.p. 217.5°–219.5° C.

| Analysis: | % C | % H | % N |
|---|---|---|---|
| Calculated for $C_{17}H_{13}NO_5$: | 65.6 | 4.2 | 4.5 |
| Found: | 65.7 | 4.1 | 4.5 |

EXAMPLE 13

Pyridine (6.5 ml.), 10.3 g. (0.115 mole) of cuprous cyanide and 22.8 g. (0.1 mole) of 7-chloro-3-phenylbenzofuran (shown at column 14, line 30, of U.S. Pat. No. 3,862,134) are heated at 220° C. for about three hours, then at 150° to 190° C. for about 16 hours. The solution is added to 40 g. of ferrous chloride hexahydrate in 65 ml. of water and 15 ml. of concentrated hydrochloric acid. The resulting mixture is heated with stirring at 90° C. for about one hour, then filtered hot. The filtrate is cooled, and the product separated by filtration. The product is heated in a boiling benzene-toluene mixture (200 ml/250 ml), then the mixture is decanted. The decantate is evaporated to half of its volume and separated from the dark, solid residue. The residues are again extracted with a boiling mixture of benzene-toluene (400 ml/200 ml), and the combined organic extracts are washed with 125 ml. 6N hydrochloric acid, water, 10 percent sodium hydroxide and water. The extracts are dried, treated with decolorizing charcoal, then evaporated to provide crude 7-cyano-3-phenylbenzofuran which is recrystallized from a mixture of benzene and petroleum ether. The white product has a m.p. 143°–145° C.

7-Cyano-3-phenylbenzofuran (45 g., 0.0206 mole) is dissolved in formic acid (580 ml plus 25 ml. water) at 85° C. At this temperature and under a nitrogen atmosphere, 30 g. of Raney nickel alloy is added. The mixture is stirred for 45 minutes at this temperature. At this time an additional 10 g. of Raney nickel is added, and two hours later an additional 5 g. of Raney nickel is added. The mixture is cooled, mixed with sulfur to inactivate the catalyst and filtered. The catalyst is washed with dichloromethane. The filtrate is diluted with water and dichloromethane. The dichloromethane solution is washed with water twice and then twice with saturated sodium bicarbonate solution and then finally again with water. The organic solution is then dried and concentrated to provide a gray solid. This solid is 3-phenyl-7-benzofurancarboxaldehyde. Its structural assignment is confirmed by its infrared spectral characteristics.

A solution of 3-phenyl-7-benzofuranylaldehyde (20 g., 0.09 mole) in 300 ml. of dichloromethane is cooled to 15° C., and bromine (14.4 g., 0.09 mole) dissolved in 15 ml. of dichloromethane is added dropwise over 15 minutes while stirring. After stirring for five minutes the reaction mixture is washed twice with saturated sodium bicarbonate solution, washed with water, and then dried over magnesium sulfate. The dichloromethane solution is then filtered to remove the magnesium sulfate and evaporated to dryness while maintaining the temperature of the mixture below 25° C. Benzene is then added, and the mixture is again evaporated under vacuum. The product is purified by column chromatography on 210 g. of fluorisil. The product is dissolved in 40 ml. of benzene and placed on a column with one liter of hexane-benzene (2:1). The product is eluted with 1:1 hexane-benzene and benzene.

The product from the preceding step, 2-bromo-3-phenyl-7-benzofurancarboxaldehyde (29.5 g., 0.098 mole), is dissolved by warming in 150 ml. of acetic acid. The mixture is cooled to 40° C. and 15.2 g. (0.12 mole) of cyclohexene is added, followed by a dropwise addition of a solution of dinitrogen tetroxide (12.6 g., 0.14 mole) dissolved in about 30 mo. of acetic acid. The mixture is heated at about 55° C. for a total of three hours. It is then cooled to room temperature, and a yellow precipitate forms which is separated by filtration. The precipitate is washed with acetic acid, then with diethyl ether. The precipitate is dissolved in dichloromethane, and the dichloromethane solution is washed with water, with saturated sodium carbonate solution, then twice with water. The dichloromethane extracts are dried over magnesium sulfate, then filtered to remove the magnesium sulfate and evaporated under vacuum to provide a yellow residue. This solid is the novel compound 2-nitro-3-phenyl-7-benzofuranaldehyde, m.p. 169°–173° C. It is used without further purification for the next step. The pure aldehyde has m.p. 174°–176° C.

A mixture of 5.1 g. (0.0191 mole) of 2-nitro-3-phenyl-7-benzofuranaldehyde, sodium acetate (2.3 g., 0.0278 mole) and acetic anhydride (9.1 g.) is heated at 145°–150° C. with stirring. After 16 hours of heating, an additional 10 ml. of acetic anhydride is added and refluxing is continued for five additional hours. The mixture is stirred into 200 ml. of water, and the residue is separated by filtration and washed with water. The residue is dissolved in a solution of 30 ml. of concentrated ammonium hydroxide in 400 ml. of water, filtered, and added to 10 percent sulfuric acid solution. An off-yellow solid is obtained which is washed with water and then with diethyl ether. The product is recrystallized twice from acetic acid, with treatment with decolorizing charcoal. The product is 2-nitro-3-phenyl-7-benzofuranacrylic acid, m.p. 281.5°–283° C.

| Analysis: | % C | % H | % N |
|---|---|---|---|
| Calculated for $C_{17}H_{11}NO_5$: | 66.0 | 3.6 | 4.5 |
| Found: | 65.8 | 3.4 | 4.4 |

EXAMPLE 14

A mixture of 2.97 g. (10 moles) of 2-nitro-3-phenyl-5-benzofuranacetic acid (shown in Example 9 hereof) in 125 ml. of methanol is warmed to effect complete solution, and 10 ml. of 1.0M sodium hydroxide solution is added. The solvent is evaporated under vacuum, benzene is added, and the mixture is again evaporated under vacuum to provide a solid residue. The crystalline residue is recrystallized from a mixture of ethanol and petroleum ether to provide a light yellow product which is washed with petroleum ether. A second recrystallization provides sodium 2-nitro-3-phenyl-5-benzofuranacetate, m.p. 270°–273° C. (dec.).

| Analysis: | % C | % H | % N |
|---|---|---|---|
| Calculated for $C_{17}H_{10}NNaO_5$: | 58.9 | 3.10 | 4.30 |
| Found: | 58.5 | 3.35 | 4.26 |

EXAMPLE 15

A mixture of 2-nitro-3-phenyl-5-benzofuranacetic acid (3.0 g., 0.010 mole), thionyl chloride (1.8 g., 0.015 mole) and 200 ml. of dichloromethane is heated to its reflux temperature and maintained at reflux for about five hours. The mixture is evaporated under vacuum to provide a residue, benzene is added to the residue, and the mixture is again evaporated under vacuum to dryness. This is repeated three more times. The residue is a yellow oil which is analyzed by infrared spectroscopy to confirm that it is 2-nitro-3-phenyl-5-benzofuranacetyl chloride.

EXAMPLE 16

A mixture of 2-nitro-3-phenyl-7-benzofuranacetic acid (2.6 g.), sulfuric acid (2.6 g.) and ethanol (25 ml.) is heated to its reflux temperature and maintained at reflux for about 16 hours. The mixture is added to 200 ml. of ice water and extracted with diethyl ether, and the ether extracts are washed with water, then three times with saturated sodium bicarbonate solution, then again with water and finally twice with saturated sodium chloride solution. The ether solution is dried over magnesium sulfate, then filtered to remove the magnesium sulfate and evaporated under vacuum. The residue is a yellow solid which is recrystallized from cyclohexane in the presence of decolorizing charcoal. The product is ethyl 2-nitro-3-phenyl-7-benzofuranacetate, m.p. 87°–88° C.

| Analysis: | % C | % H | % N |
|---|---|---|---|
| Calculated for $C_{18}H_{15}NO_5$: | 66.45 | 4.6 | 4.3 |
| Found: | 66.50 | 4.5 | 4.3 |

EXAMPLE 17

Equimolar amounts of 3-hydroxytoluene and α-bromoacetophenone are refluxed in benzene in the presence of potassium carbonate to provide α-(3-methylphenoxy)acetophenone.

A mixture of four parts by weight polyphosphoric acid to one part α-(3-methylphenoxy)acetophenone is heated at about 125° C. for several hours, then poured into an ice-water mixture. The solid product isolated by filtration is a mixture of (about 2:3) 4-methyl-3-phenylbenzofuran and 6-methyl-3-phenylbenzofuran. This mixture is treated with liquid bromine in dichloromethane to provide a mixture of 2-bromo-4-methyl-3-phenylbenzofuran and 2-bromo-6-methyl-3-phenylbenzofuran which is fractionally recrystallized. One fraction contains a 1:3 ratio of the 6 isomer to the 4 isomer. This fraction is chromatographed on a silica gel column, eluting with large volumes of petroleum ether to provide early fractions of about 85 percent 4-methyl isomer.

A mixture of 2-bromo-4-methyl-3-phenylbenzofuran and 2-bromo-6-methyl-3-phenylbenzofuran (about 15 percent 6 isomer) (51.5 g., 0.179 mole), N-bromosuccinimide (37.7 g., 0.178 mole) and benzoyl peroxide (about 0.05 g.) in 400 ml. of carbon tetrachloride is heated at its reflux temperature while shining a sunlamp on the mixture until reaction is complete. The mixture is cooled, then filtered to remove succinimide, and the organic layer is evaporated to dryness and suspended in petroleum ether. The white solid product is separated by filtration. It is about 95 percent pure 2-bromo-4-bromomethyl-3-phenylbenzofuran. The 2-bromo-4-bromomethyl-3-phenylbenzofuran (44.5 g., 0.122 mole) dissolved in acetone (165 ml.), aqueous (30 ml.) sodium cyanide (6.0 g., 0.122 mole) and ethanol (112 ml.) are mixed and heated to reflux. After about five hours of heating the mixture is allowed to stir at about 25° C. for about 16 hours. The reaction mixture is evaporated under vacuum, the residue is dissolved in diethyl ether and water-washed, and the organic layer is again concentrated to provide an oily brown solid, 2-bromo-4-cyanomethyl-3-phenylbenzofuran.

A solution of 37 g. of 2-bromo-4-cyanomethyl-3-phenylbenzofuran in 235 ml. of absolute ethanol is treated with 15 g. of potassium hydroxide in 15 ml. of water, and the mixture is refluxed for about two days. The mixture is concentrated by evaporation, water is added, and the mixture is extracted with diethyl ether. The water layer is acidified with hydrochloric acid, then this mixture is extracted with dichloromethane. The extracts are dried, then evaporated under vacuum to provide a brown residue. The residue is treated with diethyl ether and a solid forms which is separated by filtration and washed with isopropyl alcohol. The product is 2-bromo-3-phenyl-4-benzofuranacetic acid, m.p. 131°–133° C.

| Analysis: | % C | % H |
|---|---|---|
| Calculated for $C_{16}H_{11}BrO_3$: | 58.05 | 3.35 |
| Found: | 58.10 | 3.40 |

A solution of 2-bromo-3-phenyl-4-benzofuranacetic acid (12.1 g., 0.0365 mole) and cyclohexane (3.3 g., 0.04 mole) in 100 ml. of chloroform is treated with 5 g. of dinitrogen tetroxide in 20 ml. of chloroform dropwise. The mixture is stirred for 16 hours at about 25° C. then at 50°–55° C. for about 20 minutes. The mixture is washed with water, and the organic layer is treated with an aqueous base. The aqueous layer is acidified, then extracted with dichloromethane. The organic layer is washed thrice with water, dried and evaporated. Two recrystallizations from benzene give light yellow solid 2-nitro-3-phenyl-4-benzofuranacetic acid, m.p. 187.5°–189.5° C.

EXAMPLE 18

Using the method of Example 17 and starting with 2,4-dimethylphenol and α-bromoacetophenone and cyclizing at 50°–60° C., 5,7-dimethyl-3-phenylbenzofuran is obtained.

To a solution of 5 g. (0.0225 mole) of 5,7-dimethyl-3-phenylbenzofuran in 30 ml. of carbon tetrachloride and 8.0 g. (0.045 mole) of N-bromosuccinimide in 30 ml. of carbon tetrachloride is added 0.01 g. of benzoyl peroxide. The mixture is heated to its reflux temperature while irradiating with a sunlamp and maintained at reflux for about 30 minutes, cooled and filtered. The filtrate is evaporated to an oily residue. The residue is about two-thirds of the desired 2-bromo-5-bromomethyl-7-methyl-3-phenylbenzofuran according to nuclear magnetic resonance spectral analysis. This mixture is dissolved in acetone (34 ml.), and sodium cyanide (1.3 g.) in 6 ml. of ether is added. The mixture is added to 25 ml. of ethanol, heated to its reflux temperature and maintained at reflux for about 40 hours. The mixture is evaporated, the residue is treated with water and diethyl ether, and the resulting ether layer is separated, dried and evaporated. The brown oil residue is purified on a silica gel column to provide 3.9 g. of a yellow oil which is chiefly 2-bromo-5-cyanomethyl-7-methyl-3-phenylbenzofuran.

To a solution of the 2-bromo-5-cyanomethyl-7-methyl-3-phenylbenzofuran in 80 ml. of aqueous ethanol is added 4 g. of potassium hydroxide, and the mixture is heated at its reflux temperature for about 65 hours. The solvent is removed by evaporation, the residue is mixed into water, and the mixture is extracted with dichloromethane. The aqueous layer is acidified, then extracted with diethyl ether. The extracts are washed with water and saturated sodium chloride solution, dried and evaporated. The residue is recrystallized from benzene and a little hexane to give 0.89 g. of white solid 2-bromo-7-methyl-3-phenyl-5-benzofuranacetic acid, m.p. 183.5°–189° C. A solution of 2-bromo-7-methyl-3-phenyl-5-benzofuranacetic acid (0.89 g., 0.0027 mole) in 50 ml. of chloroform, 0.43 g. of cyclohexene and 0.57 g. of dinitrogen tetroxide is stirred for about 16 hours. The mixture is washed with water, extracted with saturated sodium bicarbonate solution, and the aqueous extracts are acidified. The solution is extracted with dichloromethane, and the extracts are dried and evaporated. The solid residue is recrystallized twice from 4:1 benzene:hexane to provide yellow solid 7-methyl-2-nitro-3-phenyl-5-benzofuranacetic acid m.p. 189°–191.5° C.

| Analysis: | % C | % H | % N |
| --- | --- | --- | --- |
| Calculated for $C_{17}H_{13}NO_5$: | 65.6 | 4.2 | 4.5 |
| Found: | 65.5 | 4.2 | 4.3 |

EXAMPLE 19

Using the method of Example 17 and starting with 4-hydroxytoluene and α-bromoacetophenone one obtains α-(4-methylphenoxy)acetophenone.

Using the method of Example 17 α-(4-methylphenoxy)-acetophenone is cyclized with polyphosphoric acid at 60° C. to provide 5-methyl-3-phenylbenzofuran, m.p. 144.5°–146° C.

A solution of 5-methyl-3-phenylbenzofuran (112 g., 0.538 mole) dissolved in 500 ml. of carbon tetrachloride is treated with 192 g. (1.076 mole) of N-bromosuccinimide. Benzoyl peroxide (0.1 g.) is added, and the mixture is stirred and heated to its reflux temperature while irradiating with a sunlamp. After about one hour, 0.5 g. of t-butyl hydroperoxide and 0.5 g. of cobalt stearate are added. The mixture is refluxed for about two hours, then allowed to come to room temperature. The mixture is filtered, and the filtrate is concentrated under vacuum to provide an oily yellow solid. The solid is washed with petroleum ether with scratching, and the precipitate is collected and dried. The crude product is 2-bromo-5-bromomethyl-3-phenylbenzofuran, m.p. 99°–108° C. The structural assignment is confirmed by infrared and nuclear magnetic resonance spectral analysis.

A solution of 2-bromo-5-bromomethyl-3-phenylbenzofuran (49.4 g., 0.135 mole) in 1100 ml. of acetic acid is warmed to 55° C. with 25.4 g. (0.202 mole) of cyclohex-ene-4-carboxylic acid. To this solution is added dropwise 18.6 g. (0.202 mole) of dinitrogen tetroxide in 40 ml. of acetic acid over about two hours. The precipitated product is collected by filtration, washed with cold acetic acid, water and petroleum ether. The yellow crystals of novel product, 5-bromomethyl-2-nitro-3-phenylbenzofuran, are dried to m.p. 172°–180° C.

A solution of 5-bromomethyl-2-nitro-3-phenylbenzofuran (5 g., 0.015 mole) in 95 ml. of acetone is treated with 20 ml. of ethanol, and the mixture is heated to its reflux temperature. To this mixture is added 0.015 mole of sodium cyanide dissolved in 9 ml. of water, and refluxing is continued for about two hours. The mixture is evaporated under vacuum, then dichloromethane and water are added to the residue. The organic layer is separated, washed with water and dried. The organic layer is then evaporated under vacuum. The residue is purified by eluting twice with benzene through a silica gel column, followed by refluxing in 30 ml. of diethyl ether. The yellow precipitate is separated by filtration and recrystallized twice from benzene to provide 5-cyanomethyl-2-nitro-3-phenylbenzofuran, m.p. 166°–168° C.

A one ml. portion of 50 percent sulfuric acid is added to 0.1 g. of 5-cyanomethyl-2-nitro-3-phenylbenzofuran, and the mixture is heated slowly over one hour in an oil bath to about 160° C. bath temperature. The mixture is heated at this temperature for an additional 1.5 hours, allowed to cool, and poured into water. The aqueous mixture is extracted twice with dichloromethane, the organic extracts are washed with water, dried, and evaporated under vacuum. The residue is a yellow solid, 2-nitro-3-phenylbenzofuran-5-acetic acid. Its spectral characteristics confirm that it is the same as the product obtained in Example 9.

EXAMPLE 20

Step 1. A mixture of 50 g. (0.175 mole) of 4-phenyl-α-bromoacetophenone, 30.6 g. (0.17 mole) of ethyl 4-hydroxyphenylacetate and 36 g. (0.26 mole) of potassium carbonate in 500 ml. of benzene is heated to its reflux and maintained at reflux for about 16 hours while removing water through a Dean-Stark trap. The mixture is filtered, washed with water and saturated sodium chloride solution and dried over calcium sulfate. Evaporation of the benzene provides a residue which is recrystallized from a benzene-hexane mixture, then an ethylacetate-hexane mixture to provide white plates of ethyl4-(4-phenylbenzoylmethoxy)phenylacetate. The structural assignment of the product is established by nuclear magnetic resonance spectral analysis.

Step 2. A stirred mixture containing 15 g. of the product of Step 1 and 150 g. of polyphosphoric acid is heated at about 130° C. for about 45 minutes. The mixture is poured into one liter of water and stirred. A yellow solid forms and is collected and recrystallized from a mixture of ethyl acetate and hexane to provide ethyl 3-(4-biphenylyl)-5-benzofuranacetate. The structural assignment of the product is checked by nuclear magnetic resonance spectral analysis.

Step 3. A mixture of 6.5 g. of the ester product of Step 2, 150 ml. of ethanol and 150 ml. of ten percent sodium hydroxide solution is heated on a steam cone. After about 1.5 hours most of the solid dissolves. The mixture is filtered hot, and the filtrate is cooled.

The mixture is heated on a steam cone for about 30 minutes, then acidified with 6N hydrochloric acid. The solid product is 3-(4-biphenylyl)-5-benzofuranacetic acid, m.p. 230°–233° C.

Step 4. A mixture of 1.5 g. (4.6 mmoles) of 3-(4-biphenylyl)-5-benzofuranacetic acid in 250 ml. of dichloromethane is treated with 0.5 g. (5 mmoles) of dinitrogen tetroxide, and the mixture is stirred for about 16 hours. The mixture is evaporated to dryness, and the residue is recrystallized from ethyl acetate to provide yellow crystals of 2-nitro-3-(4-biphenylyl)-5-benzofuranacetic acid, m.p. 230°–233° C.

| Analysis: | % C | % H | % N |
| --- | --- | --- | --- |
| Calculated for $C_{22}H_{15}NO_5$: | 70.8 | 4.1 | 3.7 |
| Found: | 70.7 | 4.1 | 3.7 |

EXAMPLE 21

Using the method of Example 20 and starting with α-bromo-3-methoxy-acetophenone and ethyl 4-hydroxyphenylacetate one obtains 3-(3-methoxyphenyl)-2-nitro-5-benzofuranacetic acid.

| Analysis: | % C | % H | % N |
| --- | --- | --- | --- |
| Calculated for $C_{17}H_{13}NO_6 \cdot \frac{1}{2}H_2O$: | 60.7 | 4.2 | 4.2 |
| Found: | 60.7 | 3.8 | 4.4 |

EXAMPLE 22

Starting with 4-bromo-α-bromoacetophenone and 4-hydroxyphenylacetic acid and using the method of Example 2, Steps 1 and 2, one obtains ethyl 3-(4-bromophenyl)-5-benzofuranacetate.

A mixture of 20 g. (0.056 mole) of ethyl 3-(4-bromophenyl)-5-benzofuranacetate, 6.0 g. (0.067 mole) of cuprous cyanide and 5 ml. of pyridine is stirred under a nitrogen atmosphere while heating with an oil bath at 150° to 160° C. for about 18 hours. The reaction mixture is then poured into a mixture of 18 g. of ferric chloride, 10 ml. of concentrated hydrochloric acid and 50 ml. of water. The mixture is heated on a steam cone for about 1.5 hours, extracted with diethyl ether and the extracts washed with 6N hydrochloric acid, 10 percent sodium hydroxide and saturated sodium chloride solution. The dried solution is filtered, evaporated to about 25 ml., and hexane is added. The product is collected, dissolved in diisopropyl ether and treated with decolorizing charcoal. The filtrate is evaporated to 50 ml., and the precipitate, ethyl 3-(4-cyanophenyl)-5-benzofuranacetate is collected.

To a solution of 2.5 g. (8.2 mmoles) of the ester in 75 ml. of methanol, 0.48 g. (8.2 mmoles) of 85 percent potassium hydroxide is added, and the mixture is stirred for about 16 hours. The solution is diluted with 75 ml. of water, the acidified with hydrochloric acid. The precipitate is separated, dissolved in boiling chloroform and dried. Hexane is added to the solution until the product, 3-(4-cyanophenyl)-5-benzofuranacetic acid, precipitates.

A solution of 1.0 g. of 3-(4-cyanophenyl)-5-benzofuranacetic acid and 1 g. of dinitrogen tetroxide in 200 ml. of dichloromethane is stirred for about 16 hours. Evaporation of the reaction mixture leaves a residue which is dissolved in chloroform. The solution is placed on a column of 50 g. of silica gel for chromatography. Elution with chloroform provides the desired product as a yellow crystalline solid, 3-(4-cyanophenyl)-2-nitro-5-benzofuranacetic acid, m.p. 220°-222° C.

The compounds of the following table are prepared using the synthetic method described in Example 20, starting with 4-hydroxyphenylacetic acid and the appropriate known substituted α-bromoacetophenone.

| Example Number | Starting Material | Product | Melting Point (in °C.) |
|---|---|---|---|
| 23 | 3,4-dimethylphenacyl bromide | 3-(3,4-dimethylphenyl)-2-nitro-5-benzofuranacetic acid | 200–203 |
| 24 | 3-trifluoromethylphenacyl bromide | 3-(3-trifluoromethylphenyl)-2-nitro-5-benzofuranacetic acid | 181–184 |
| 25 | 2-fluorophenacyl bromide | 3-(2-fluorophenyl)-2-nitro-5-benzofuranacetic acid | 190–193 |
| 26 | 4-nitrophenacyl bromide | 3-(4-nitrophenyl)-2-nitro-5-benzofuranacetic acid | 239–241 |
| 27 | 3,4-dichlorophenacyl bromide | 3-(3,4-dichlorophenyl)-2-nitro-5-benzofuranacetic acid | 139–141 |

-continued

| Example Number | Starting Material | Product | Melting Point (in °C.) |
|---|---|---|---|
| 28 | 4-bromophenacyl bromide (BrC6H4-CO-CH2Br) | 5-(carboxymethyl)-2-nitro-3-(4-bromophenyl)benzofuran (HOOCCH2-benzofuran-NO2, 4-Br-phenyl) | 230–233 |
| 29 | 4-fluorophenacyl bromide (FC6H4-CO-CH2Br) | 5-(hydroxymethyl)-2-nitro-3-(4-fluorophenyl)benzofuran (HOOCH2-benzofuran-NO2, 4-F-phenyl) | 204–206 (dec.) |

EXAMPLE 30

Thionyl chloride is reacted with 2-nitro-3-phenylbenzofuran-5-acetic acid (shown in Example 9 hereof) to provide 2-nitro-3-phenyl-5-benzofuranacetyl chloride.

A mixture of 3 g. of 2-nitro-3-phenyl-5-benzofuranacetyl chloride and 30 ml. of ethylene glycol in 130 ml. of chloroform is heated to its reflux temperature and maintained at reflux temperature for 3.5 hours. The mixture is then extracted thrice with water and washed with saturated sodium bicarbonate solution, twice with water and once with saturated sodium chloride solution. The organic layer is dried, then evaporated to provide a residue which solidifies. Recrystallization from 1:1 cyclohexane-benzene, then benzene and finally ethanol provides 2-hydroxyethyl 2-nitro-3-phenyl-5-benzofuranacetate, m.p. 104°–107° C.

EXAMPLE 31

A mixture of 2.59 g. (8.2 mmoles) of 2-nitro-3-phenyl-5-benzofuranacetyl chloride in 35 ml. of benzene is treated with 1.46 g. (16.4 mmoles) of N,N-dimethylaminoethanol. After stirring for about 64 hours, the mixture is washed twice with water, then the organic layer is evaporated to provide a residue. The residue is dissolved in chloroform and chromatographed on silica gel. Infrared and nuclear magnetic resonance spectral analysis are consistent with the desired product, N,N-dimethylaminoethyl 2-nitro-3-phenyl-5-benzofuranacetate. This free base is reacted with perchloric acid in diethyl ether to provide a solid product which is found to be perchloric acid salt.

| Analysis: | % C | % H | % N |
|---|---|---|---|
| Calculated for $C_{20}H_{20}N_2O_5 \cdot HClO_4 \cdot \frac{1}{2}H_2O$: | 50.7 | 4.4 | 5.9 |
| Found: | 50.7 | 4.5 | 5.5 |

EXAMPLE 32

To a solution of 2.08 g. (8.25 mmoles) of 3-phenyl-7-benzofuranacetic acid in 10 ml. of benzene at 60° C. is slowly added small portions of yellow mercuric oxide (1.45 g., 6.7 mmoles) and iodine (2.09 g., 8.25 mmoles). After about two hours the mixture is filtered, then the filtrate is evaporated to dryness to provide 2-iodo-3-phenyl-7-benzofuranacetic acid.

To a solution of 2.2 g. (5.8 mmoles) of 2-iodo-3-phenyl-7-benzofuranacetic acid, 1 g. (5.8 mmoles) of cyclohexene and 175 ml. of chloroform is added 0.9 g. (10 mmoles) of dinitrogen tetroxide in 15 ml. of chloroform. The mixture is stirred for 20 hours, washed with water and made basic with sodium hydroxide. The chloroform layer is acidified with hydrochloric acid, washed with water twice and dried, then evaporated to provide 2-nitro-3-phenyl-7-benzofuranacetic acid, identical to the sample prepared in Example 2.

Using the method of Example 20, the following intermediate acids and final product compounds of Formula I are prepared starting with knwon substituted acetophenones or acetophenones prepared by known methods and ethyl 4-hydroxyphenylacetate. The acetophenones are treated with one equivalent of bromine in methylene chloride to obtain the required phenacylbromides.

| Example No. | Starting Acetophenone | Melting Point of Intermediate Acid (°C.) | Product | Melting Point of Product (°C.) |
|---|---|---|---|---|
| 33 | 2-chloroacetophenone (O=C-CH3, 2-Cl-phenyl) | 130–134 | HOOCCH2-benzofuran-NO2, 2-Cl-phenyl | 164–167 |
| 34 | 2,4-dichloroacetophenone (O=C-CH3, 2,4-di-Cl-phenyl) | — | HOOCCH2-benzofuran-NO2, 2,4-di-Cl-phenyl | 165–167 |

-continued

| Example No. | Starting Acetophenone | Melting Point of Intermediate Acid (°C.) | Product | Melting Point of Product (°C.) |
|---|---|---|---|---|
| 35 | 2,4-dichloro acetophenone (O=C−CH₃ with 2-Cl, 4-Cl on phenyl) | 138–140 | HOOCCH₂-benzofuran-3-(2,4-dichlorophenyl)-2-NO₂ | 175–177 |
| 36 | 3-fluoro acetophenone | — | HOOCCH₂-benzofuran-3-(3-fluorophenyl)-2-NO₂ | 185–187 |
| 37 | 3-chloro acetophenone | — | HOOCCH₂-benzofuran-3-(3-chlorophenyl)-2-NO₂ | 173–176 |
| 38 | 3-bromo acetophenone | — | HOOCCH₂-benzofuran-3-(3-bromophenyl)-2-NO₂ | 176–177 |
| 39 | 3-nitro acetophenone | 149–151 | HOOCCH₂-benzofuran-3-(3-nitrophenyl)-2-NO₂ | 193–195 |

EXAMPLE 40

Equimolar amounts of 3-bromo-4-hydroxytoluene and α-bromoacetophenone are refluxed in benzene in the presence of potassium carbonate to provide α-(2-bromo-4-methylphenoxy)acetophenone in the usual manner.

A mixture of 700 g. of polyphosphoric acid and 100 g. of α-(2-bromo-4-methylphenoxy)acetophenone is heated at 80°–90° C. for two hours, then poured into two liters of water with stirring. Chloroform (1 liter) is added, and the phases are separated. The organic layer is washed with water, dried, then evaporated to provide 7-bromo-5-methyl-3-phenylbenzofuran as a brown oil.

A solution of 86.6 g. (0.30 mole) of 7-bromo-5-methyl-3-phenylbenzofuran in 600 ml. of dichloromethane is treated dropwise over 45 minutes with 47.9 g. (0.30 mole) of bromine. After stirring one additional hour, the mixture is washed once with water (300 ml.) and thrice with 300 ml. portions of saturated sodium bicarbonate solution, dried, then evaporated to provide 2,7-dibromo-5-methyl-3-phenylbenzofuran as an oil which crystallizes from hexane.

A mixture containing 68.7 g. (0.19 mole) of 2,7-dibromo-5-methyl-3-phenylbenzofuran and 35.5 g. (0.19 mole) of N-bromosuccinimide in one liter of carbon tetrachloride is irradiated with a bulb simulating sunlight for two hours. An additional 10 g. of N-bromosuccinimide is added, and irradiation is continued for one hour. The mixture is cooled and filtered. The filtrate is evaporated to a brown oil which crystallizes when triturated with hexane to provide solid 5-bromomethyl-2,7-dibromo-3-phenylbenzofuran.

A solution of 17.8 g. (0.040 mole) of 5-bromomethyl-2,7-dibromo-3-phenylbenzofuran in 150 ml. of N,N-dimethylformamide, 2.0 g. (0.04 mole) of sodium cyanide and 15 ml. of water is heated on a steam bath for 1.5 hours. The mixture is poured into one liter of water and stirred for about 16 hours. The mixture is extracted with 500 ml. of ethyl acetate, the extracts washed with water, then dried. Evaporation followed by trituration with hexane-ethyl acetate gives 5-cyanomethyl-2,7-dibromo-3-phenylbenzofuran as a white solid.

A solution containing 11.1 g. (0.028 mole) of 5-cyanomethyl-2,7-dibromo-3-phenylbenzofuran, 10.7 g. (0.11 mole) of dinitrogen tetroxide, 13.9 g. (0.11 mole) of cyclohexene-4-carboxylic acid and 1 g. of iodine in 500 ml. of chloroform is stirred at room temperature for 16 hours. An additional 13.9 g. of cyclohexene-4-carboxylic acid and 10.7 g. of dinitrogen tetroxide are added, and stirring is continued for 16 hours. The reaction is then treated with 500 ml. of 10 percent sodium thiosulfate. The phases are separated, and the organic phase is washed thrice with 250 ml. portions of saturated sodium bicarbonate, once with 250 ml. of 3N hydrochloric acid and dried. Evaporation gives 7-bromo-5-cyanomethyl-2-nitro-3-phenylbenzofuran as a yellow solid, recrystallized from ethyl acetate-hexane to give a sample for analysis.

| Analysis: | % C | % H | % N |
|---|---|---|---|
| Calculated for $C_{16}H_9BrN_2O_3$: | 53.8 | 2.5 | 7.8 |
| Found: | 54.1 | 2.5 | 7.8 |

A mixture containing 2.0 g. of 7-bromo-5-cyanomethyl-2-nitro-3-phenylbenzofuran and 30 ml. of 1:1 sulfuric acid and water is stirred and heated at 150° C. for 1.5 hours. The mixture is then poured into 200 ml. of water.

The solid is separated by filtration, washed with water and dried. Recrystallization from ethanol gives yellow crystals of 7-bromo-2-nitro-3-phenyl-5-benzofuranacetic acid, m.p. 125°–127° C.

| Analysis: | % C | % H | % N |
|---|---|---|---|
| Calculated for $C_{16}H_{10}BrNO_5$: | 51.1 | 2.7 | 3.7 |
| Found: | 50.6 | 2.7 | 4.0 |

EXAMPLE 41

Using the method described in Example 17, equimolar amounts of 2-hydroxy-4-methoxytoluene and α-bromo-2-fluoroacetophenone are refluxed in benzene in the presence of potassium carbonate to provide 2-fluoro-α-(2-methyl-5-methoxyphenoxy)acetophenone. Recrystallization from cyclohexane provides a tan solid, m.p. 57°–58° C.

Cyclization of 16.4 g. of 2-fluoro-α-(2-methyl-5-methoxyphenoxy)acetophenone is carried out in polyphosphoric acid (120 g.) by heating at 60° C. for thirty minutes. The reaction mixture is poured into water and extracted with diethyl ether to provide 3-(2-fluorophenyl)-7-methyl-4-methoxybenzofuran as a brown oil. Its structure is confirmed by nuclear magnetic resonance and infrared spectral analysis.

Using the method of Example 17, 3-(2-fluorophenyl)-7-methyl-4-methoxybenzofuran is brominated with N-bromosuccinimide to provide 2-bromo-7-bromomethyl-3-(2-fluorophenyl)-4-methoxybenzofuran as an oil. Its structure is assigned on the basis of nuclear magnetic resonance and infrared spectral analysis.

Using the method of Example 17, 2-bromo-7-bromomethyl-3-(2-fluorophenyl)-4-methoxybenzofuran is reacted with sodium cyanide to provide 2-bromo-7-cyanomethyl-3-(2-fluorophenyl)-4-methoxybenzofuran as a brown solid after isolation by column chromatography.

2-Bromo-7-cyanomethyl-3-(2-fluorophenyl)-4-methoxybenzofuran is hydrolyzed by refluxing in ethanolic sodium hydroxide for 6 hours. Extraction with diethyl ether provides 2-bromo-3-(2-fluorophenyl)-4-methoxy-7-benzofuranacetic acid as a white solid after recrystallization from benzene, m.p. 188°–191.5° C.

Using the method of Example 17, 2-bromo-3-(2-fluorophenyl)-4-methoxy-7-benzofuranacetic acid is reacted with dinitrogen tetroxide to provide 3-(2-fluorophenyl)-4-methoxy-2-nitro-7-benzofuranacetic acid. Recrystallization of the acid from benzene provides yellow crystals, m.p. 185°–195° C.

| Analysis: | % C | % H | % N |
|---|---|---|---|
| Calculated for $C_{17}H_{12}FNO_6$: | 59.1 | 3.5 | 4.1 |
| Found: | 58.4 | 3.3 | 3.7 |

What is claimed is:

1. A compound of the formula

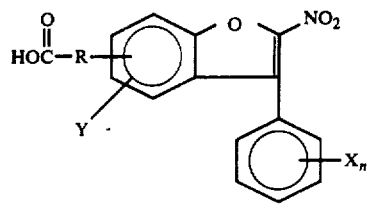

wherein X is halogen, lower alkyl, lower alkoxy, nitro, phenyl, cyano or trifluoromethyl, n is zero, one or two, R is straight or branched chain alkylene of one to four carbon atoms or ethenylene, Y is methyl, methoxy, halogen or hydrogen or an ester, amide, acyl halide or pharmaceutically acceptable salt thereof, the ester and amide portions of those derivatives containing not more than ten carbon atoms said ester being selected from the group consisting of lower alkyl esters, hydroxyalkyl esters, N,N-dialkylaminoalkyl esters, glyceryl esters and alkoxyalkyl esters and said amides being selected from the group consisting of N-unsubstituted amides, N-alkylamides, N-N-dialkylamides, dialkylaminoalkylamides, quaternary ammonium alkylamides, bis(2-hydroxyethyl) amides, amino acid amides, carboxyphenylamides, piperazinyl amides amino sugar amides, alkylsulfonamides, sulfoethylamides, sulfamoylphenylamides, and 5-tetrazolylamides.

2. A compound according to claim 1 wherein R is methylene.

3. A compound according to claim 1 wherein each X is fluorine and/or chlorine.

4. A compound according to claim 1 wherein the 4 position of the benzofuran moiety is unsubstituted.

5. An alkali metal salt according to claim 1.

6. A compound according to claim 1 wherein n is zero.

7. A compound according to claim 1 wherein n is one.

8. A compound of the formula

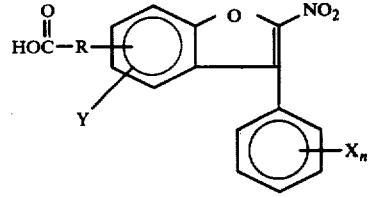

wherein X is halogen, lower alkyl, lower alkoxy, nitro, phenyl, cyano or trifluoromethyl, n is zero, one or two, R is straight or branched chain alkylene of one to four carbon atoms or ethenlene and Y is methyl, methoxy, halogen or hydrogen.

9. The compound 2-nitro-3-phenyl-7-benzofuranacetic acid, according to claim 8.

10. The compound 2-nitro-3-phenyl-6-benzofuranacetic acid according to claim 8.

11. The compound 2-nitro-3-phenyl-5-benzofuranacetic acid according to claim 8.

12. The compound 2-nitro-3-phenyl-7-benzofuranacrylic acid according to claim 8.

13. The compound 2-nitro-3-phenyl-5-benzofuranpropionic acid according to claim 8.

14. The compound 2-nitro-3-phenyl-7-benzofuranpropionic acid according to claim 8.

15. 3-(4'-Chlorophenyl)-2-nitro-5-benzofuranacetic acid according to claim 8.
16. 3-(4'-Fluorophenyl)-2-nitro-7-benzofuranacetic acid according to claim 8.
17. 3-(4'-Chlorophenyl)-2-nitro-7-benzofuranacetic acid according to claim 8.
18. A lower alkyl ester according to claim 1.
19. A hydroxyalkyl ester according to claim 1.
20. An N,N-dialkylaminoalkyl ester according to claim 1.
21. A glyceryl ester according to claim 1.
22. An alkoxyalkyl ester according to claim 1.
23. An N-unsubstituted amide according to claim 1.
24. An N-alkylamide according to claim 1.
25. An N,N-dialkylamide according to claim 1.
26. A dialkylaminoalkylamide according to claim 1.
27. A quaternary ammonium alkylamide according to claim 1.
28. A bis(2-hydroxyethyl)amide according to claim 1.
29. An amino acid amide according to claim 1.
30. A carboxyphenylamide according to claim 1.
31. A piperazinyl amide according to claim 1.
32. An amino sugar amide according to claim 1.
33. An alkylsulfonamide according to claim 1.
34. A sulfoethylamide according to claim 1.
35. A sulfamoylphenylamide according to claim 1.
36. A 5-tetrazolylamide according to claim 1.
37. A method for arresting or inhibiting the growth of microorganisms comprising contacting microorganisms with a compound according to claim 1 in an amount sufficient to inhibit the growth of said microorganisms.
38. A method according to claim 37 for arresting or inhibiting the growth of bacteria.
39. A method for arresting or inhibiting the growth of trichomonads comprising contacting trichomonads with a compound according to claim 1 in an amount sufficient to arrest or inhibit the growth of said trichomonads.
40. An antimicrobial composition comprising an antimicrobially effective amount of a compound according to claim 1 dispersed in a pharmaceutically acceptable extending medium.

* * * * *